(12) United States Patent
Turner et al.

(10) Patent No.: US 10,048,229 B2
(45) Date of Patent: Aug. 14, 2018

(54) MATERIAL INSPECTION DEVICE

(71) Applicant: BAE SYSTEMS plc, London (GB)

(72) Inventors: Alan Raymond Turner, Barrow-in-Furness (GB); David Mathew Cummings, Barrow-in-Furness (GB); Andrew David John Nixon, Barrow-in-Furness (GB)

(73) Assignee: BAE SYSTEMS plc, London (GB)

( * ) Notice: Subject to any disclaimer, the term of this patent is extended or adjusted under 35 U.S.C. 154(b) by 200 days.

(21) Appl. No.: 14/905,917

(22) PCT Filed: Jul. 14, 2014

(86) PCT No.: PCT/GB2014/052138
§ 371 (c)(1),
(2) Date: Jan. 18, 2016

(87) PCT Pub. No.: WO2015/008046
PCT Pub. Date: Jan. 22, 2015

(65) Prior Publication Data
US 2016/0178582 A1 Jun. 23, 2016

(30) Foreign Application Priority Data

Jul. 18, 2013 (EP) ..................................... 13275167
Jul. 18, 2013 (GB) ..................................... 1312841.8

(51) Int. Cl.
*G01N 29/265* (2006.01)
*G01N 29/04* (2006.01)
(Continued)

(52) U.S. Cl.
CPC ........... *G01N 29/04* (2013.01); *B23K 31/125* (2013.01); *G01N 29/223* (2013.01);
(Continued)

(58) Field of Classification Search
CPC .... G01N 29/04; G01N 29/223; G01N 29/225; G01N 29/262; G01N 29/26;
(Continued)

(56) References Cited

U.S. PATENT DOCUMENTS 3,575,044 A * 4/1971 Gibbs ................ G01N 29/0636
228/104
3,934,457 A 1/1976 Clark et al.
(Continued)

FOREIGN PATENT DOCUMENTS

CN 103018326 A 4/2013
EP 1130385 A2 9/2001
(Continued)

OTHER PUBLICATIONS

International Search Report and Written Opinion received for Patent Application No. PCT/GB2014/052138, dated Aug. 21, 2014. 8 pages.
(Continued)

*Primary Examiner* — Manish S Shah
*Assistant Examiner* — Rose M Miller
(74) *Attorney, Agent, or Firm* — Finch & Maloney PLLC

(57) ABSTRACT

The invention relates to a surface inspection device; more specifically to the inspection of complex geometry welded joints.
There is provided a device suitable for structural health monitoring of a surface said device comprising; a guide rail and a platform comprising at least one sensor, wherein said platform is cooperatively engaged with said guide rail, when said platform traverses along the rail.

24 Claims, 5 Drawing Sheets

Figure 1:
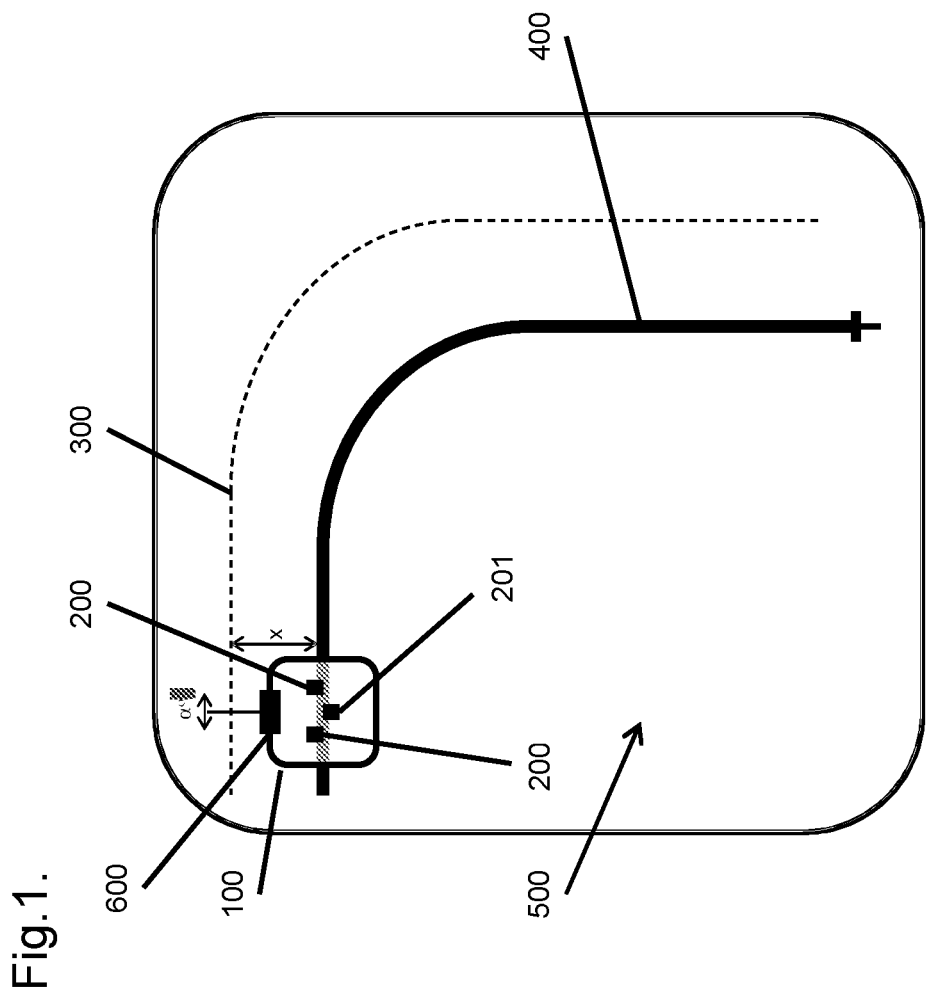

(51) Int. Cl.
*B23K 31/12* (2006.01)
*G01N 29/26* (2006.01)
*G01N 29/22* (2006.01)

(52) U.S. Cl.
CPC ......... *G01N 29/225* (2013.01); *G01N 29/262* (2013.01); *G01N 2291/0234* (2013.01); *G01N 2291/0289* (2013.01); *G01N 2291/267* (2013.01)

(58) Field of Classification Search
CPC ... G01N 2291/0234; G01N 2291/0289; G01N 2291/267; G01N 2291/2634; B23K 31/125
USPC ......... 73/588, 592, 918, 622, 621, 633, 634, 73/637, 640, 866.5, 432.1, 18, 432.16
See application file for complete search history.

(56) References Cited

U.S. PATENT DOCUMENTS

| | | | |
|---|---|---|---|
| 4,383,448 A | | 5/1983 | Fujimoto et al. |
| 4,472,346 A | * | 9/1984 | Takeda ................. G21C 17/032 376/246 |
| 4,494,907 A | * | 1/1985 | Coussau ............... F22B 37/005 324/220 |
| 4,855,678 A | * | 8/1989 | Kreiskorte ............. G01B 7/023 269/266 |
| 5,323,962 A | * | 6/1994 | Jassby ................ B23K 37/0533 105/29.1 |
| 6,530,278 B1 | | 3/2003 | Bowersox et al. |
| 2012/0204645 A1 | | 8/2012 | Crumpton et al. |

FOREIGN PATENT DOCUMENTS

| | | |
|---|---|---|
| JP | S5786045 A | 5/1982 |
| JP | S57179744 A | 11/1982 |
| JP | S59190656 A | 10/1984 |
| JP | S6230952 A | 2/1987 |
| JP | H11304772 A | 11/1999 |
| JP | 2001305116 A | 10/2001 |
| WO | 2015008046 A1 | 1/2015 |

OTHER PUBLICATIONS

GB Intellectual Property Office Search Report under Section 17(5) received for GB Patent Application No. 1312841.8 dated Nov. 26, 2013. 4 pages.

Extended European Search Report received for EP Patent Application No. 13275167.8 dated Sep. 16, 2013. 5 pages.

International Preliminary Report on Patentability received for Patent Application No. PCT/GB2014/052138, dated Jan. 28, 2016. 6 pages.

\* cited by examiner

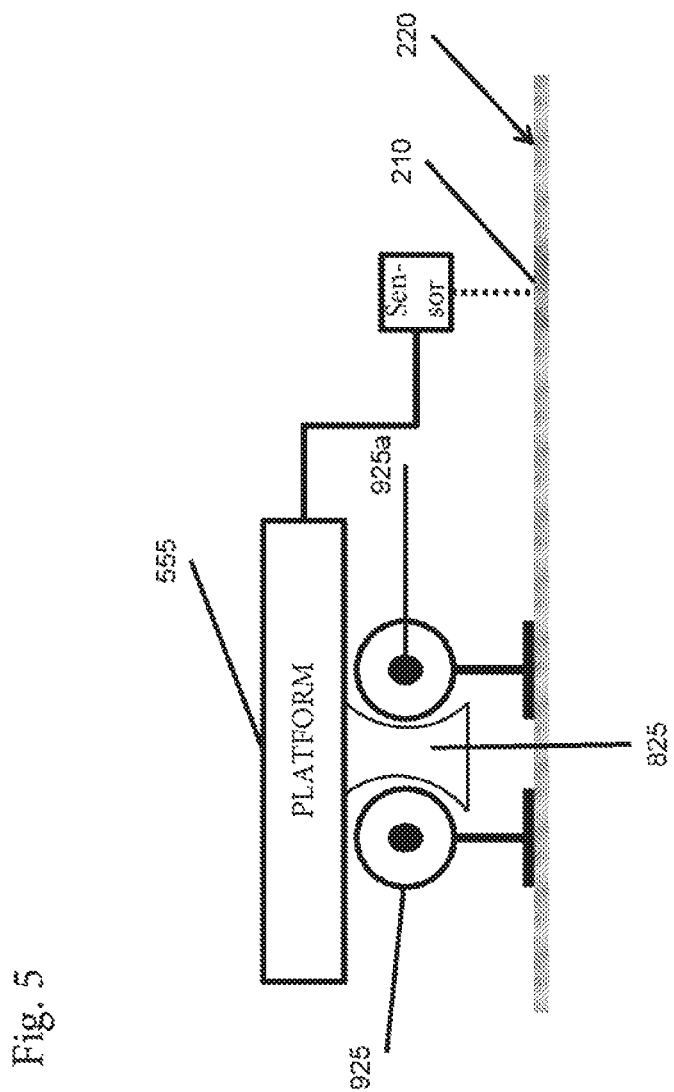

MATERIAL INSPECTION DEVICE

The invention relates to a material inspection device; more specifically to the inspection of complex geometry welded joints.

Within the field of structural health monitoring, there are a number of sensors capable of identifying flaws in a material's integrity. In some arrangements a sensor may be required to be kept at a set distance from the identified area of inspection or at a specific orientation, which needs to be maintained throughout an inspection period. These issues are compounded when the need to maintain a high level of accuracy is required as with areas such as safety critical systems and when carrying out material inspection over a surface with many contours or obstacles that may obstruct the sensor or its positioning.

In order to conduct accurate inspection on a joint such as a weld there are a number of methods currently used within industry. These range from x-ray, ultrasonic, acoustic sensors, machine vision analysis or peel test inspections; however each method comes with inherent positive and negative attributes depending on the industry, and fashion with which they are employed. One key requirement that all sensors share is the need to produce an accurate\reproducible reading of an area of inspection to provide the most reliable information to an operator.

According to a first aspect of the invention there is provided a device suitable for structural health monitoring of a material said device comprising; a guide rail mounted on a surface of said material; a platform comprising at least one sensor, wherein said platform is cooperatively engaged with said guide rail, when said platform traverses along the rail.

The invention may be utilised in a number of fields where material inspection is required, such as painted surface inspection, adhesive joints or surface monitoring, one particular utility of the invention is in the field of material joint inspection, particularly in the field of submarine construction. In the industry of submarine construction there is a need to ensure that sheets of metal that have been joined together using a weld are of sufficient quality to withstand the pressures encountered by such subsurface vessels. As a result weld joints are inspected for faults using a phased array ultrasonic sensor, this allows points of weakness to be identified and corrected. The sensor is chosen for use as it provides the most reliable information on a weld's condition, however in order to give an accurate reading the sensor must be kept at a set distance from the welds centre-line and at a set angle, which may be very narrow, such as for example +−2 degrees from the normal of the output of the ultrasound transducer, such that reflected ultrasound waves are picked up by the transducer). Both of these requirements have a tight tolerance, which if exceeded could result in key information being missed or providing inaccurate results. The tight tolerance factor presents a high probability for sensor error, especially as welding is currently inspected free hand by an engineer who may be conducting the inspection over an uneven surface and around multiple obstacles.

The device is suitable for the carriage of a sensor over a surface in a fashion that allows control over the sensor's position with respect to the weld joint.

The guide rail provides a consistent position with relation to the surface for the platform. The guide rail may be constructed from any suitable material, such as, for example a metal, an alloy, a polymer, composite or natural materials.

The guide rail guides the platform adjacent to the material joint. The guide rail may be required to be pre-shaped, malleable or flexible to avoid obstacles, follow curved joints and cope with surface undulation. Similarly each inspection area may vary in terms of its length, and as a result there is a desire for the guide rail to be extendable in order to adapt to the surface, where required, while still maintaining its rigid form to support the platform. In a preferred arrangement the guide rail may comprise at least two segments, preferably a plurality of segments. The plurality of segments may preferably be mounted coaxially on a cord or wire under compression such that the rail is substantially rigid, after its segments have been arranged in a selected configuration. They are then such that movement of the platform does not cause the rail to deviate from the selected configuration.

The segments may comprise a concave and convex end, such that they cooperatively engage with each other. Upon tensioning the cord or wire the segments are placed under compression and the guide rail becomes rigid so as to support the platform. Reducing the tension allows the guide rail to be shaped around obstacles. The guide rail may be extended by the addition of further segments. The guide rail construction chosen to accomplish the necessary requirements could also be satisfied by using a number of singular rods or elongate segments on a tensioned wire.

The guide rail may comprise at least one leg support. The leg may comprise at least one fixing mount with which to attach the leg to the surface of a material. The legs and feet provide a consistent height for the guide rail, and provide a means to attach the guide rail to the surface of the material to be inspected. The guide rail provides accurate results by ensuring that the attached platform, and hence the sensor is prevented from rotation beyond the optimum operating conditions of said sensor. The attachment to the surface may be achieved via a number of various methods and may be reversible or irreversible, whilst providing that the guide rail does not detach or move during inspection. In a preferred arrangement the fixing means is reversible, such that it can be removed from the surface, such as, for example a magnetic or electro-magnet, suction cups, Velcro, or clamps depending on surface texture with which it is to be joined. The guide rail may be mounted on the surface using an irreversible fixing means, such as, for example a chemical, such as an adhesive or mechanical fixing for example rivets, or bolts.

The sensor housing provides a stable platform for the chosen sensor, and a means for the sensor to cooperatively engage with the guide rail. The sensor housing may be constructed from any suitable material, such as, for example a metal, an alloy, a polymer, composite or natural materials.

In a preferred arrangement the platform reversibly attaches to the guide rail such as, for example by two guide rollers and a third biased guide roller. The bias may comprise at least one spring to pull the roller in to contact with the rail, this allows the platform to move freely along the guide rail whilst providing sufficient grip to support the platform and sensor weight. As the rollers rotate on a central axle a mechanical restraint such as a nut or screw may be used to tighten the biased roller onto the guide rail if a greater grip on the guide rail is required. In an alternative arrangement there may be at least two guide rails wherein said platform is cooperatively engaged with both rails. In this arrangement where the rollers may be located on the centre of the housing; this may be utilised if the weight of the sensor is substantial or if multiple sensors are used.

In the field of material inspection, gathering information on the condition of various metal weld joints, as well as identifying the presence of a fault, it is also a requirement to know the location of the fault. In a preferred arrangement the platform comprise a distance measuring device to record the distance (or time) that the platform has travelled along the rail, such as, for example a rotary encoder, attached to a guide wheel, however an alternative arrangement may utilise a click wheel, string pedometer, or even a laser interferometer, alternatively a basic timer may be started at the beginning of an inspection period. The device may also comprise a propulsion device such as to propel said platform along the guide rail, this may simply be a human pushing the platform or a motor powering the platform along the guide rail.

Figure 2:
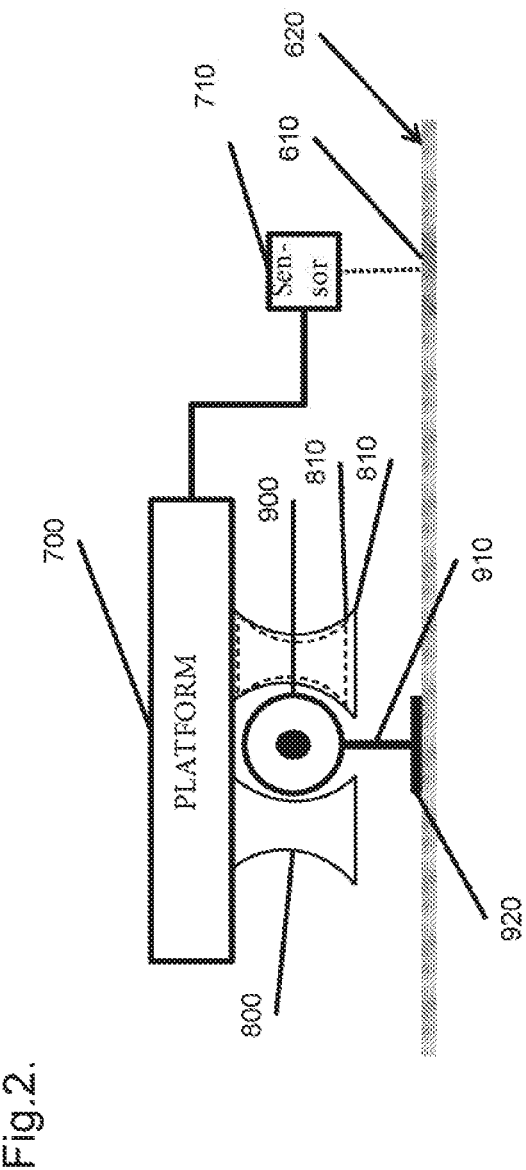
Figure 3:
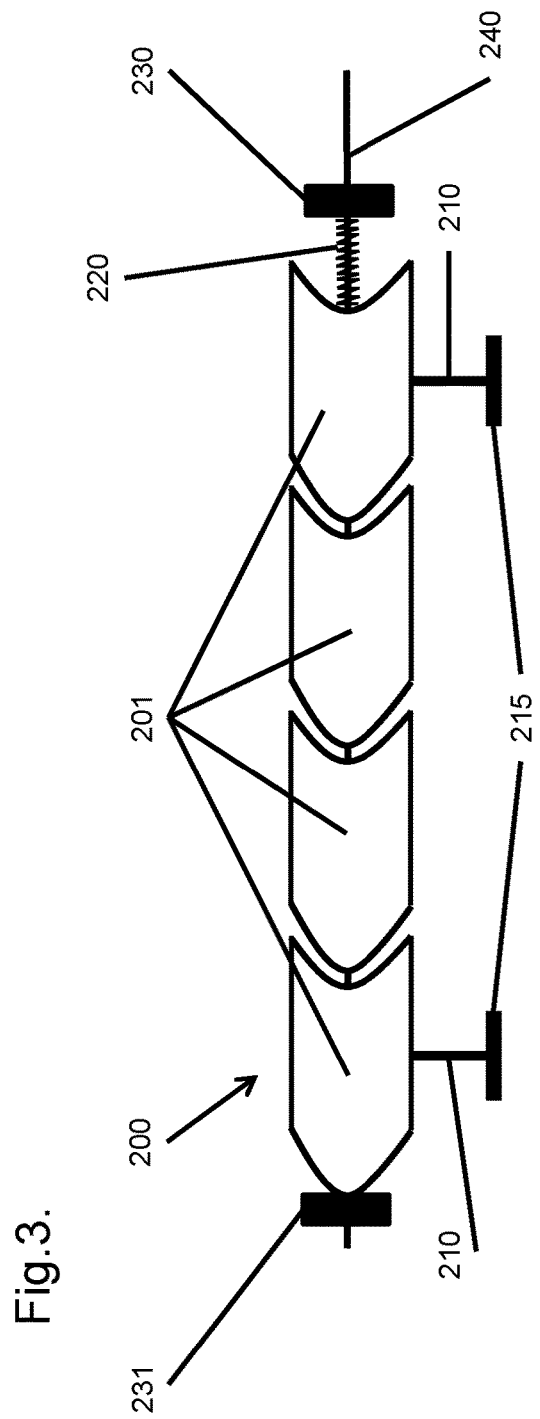
Figure 4:
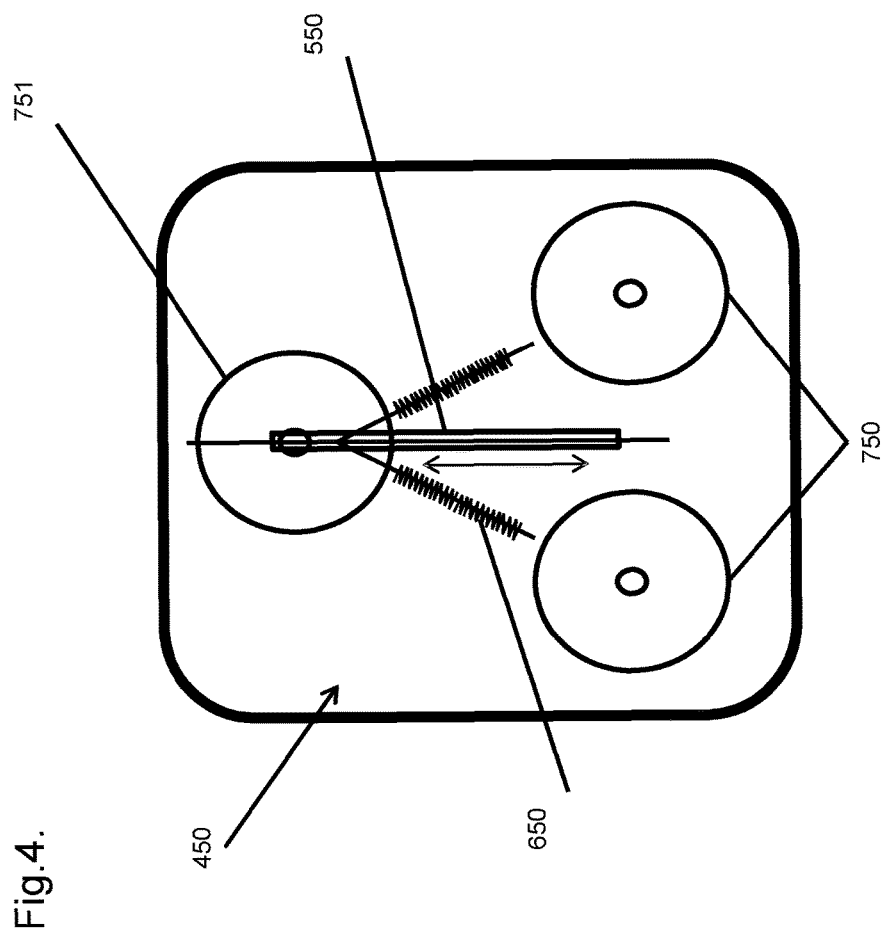

The invention will now be described by way of example with reference to the accompanying drawings, wherein:

FIG. 1 shows a plan view of the carrier and rail.
FIG. 2 shows a side view of the rail and carrier.
FIG. 3 shows a side view of a segmented rail.
FIG. 4 shows the sensor mounting platform.
FIG. 5 shows an alternative embodiment of the guide rail and carrier arrangement.

Referring to FIG. 1, there is a surface 500 of material to be inspected, in this case a metal surface. A guide rail 400 is mounted on the surface 500. A platform 100 is cooperatively engaged with the guide rail 400 by way of guide rollers 200 and a bias roller 201, which can be located underneath the platform. The guide rail 400 follows the length of the joint 300 to be inspected, which in this instant is a welded joint; the guide rail 400 lies close to and follows the weld joint 300 direction at a fixed distance X from the weld joint, providing coverage over the full length of the weld joint to be inspected. The distance X from the weld joint is dictated by the type of sensor required for use, for this example an ultrasonic sensor 600 is located on the platform 100, such that it is at a fixed distance X to the platform 100.

The guide rail 400 is typically on or very close to the weld 300 and so is placed on the material 500 at a position as required by the sensor that will achieve the most accurate results. The sensor is located on the platform 700 and the platform 700 is forced to only follow the path of the guide rail 400, this enables the sensor to be guided along the welded joint 300 to be inspected. The guide rail 400 may need to be placed in between protruding obstacles, around tight bends or across undulating surfaces, whilst keeping distance X, as constant as possible. As well as maintaining the correct distance X, the guide rail 400 will keep the sensor at the correct orientation α° by utilising the guide wheels 200, bias wheel 201 and platform 100.

In FIG. 2 the platform 700 is mounted onto the guide rail 900 utilising the bias created by the bias roller 800 and guide rollers 810. The guide rail 900 supports the platform 700 and keeps the sensor 710 a fixed distance from the weld of the material 620 by means of the legs 910 and the fixing mounts 920. In this configuration the fixing mounts 920 are a magnet, which allows a reversible attachment to the metal surface 620. The position of the sensor 710 to the material joint area 610 may then be kept at a fixed distance and attitude as the platform moves along the guide rail 900. The bias roller provides the grip required to attach the platform 700 to guide rail 900 as this impacts the smooth movement of the platform, as well as the ability to remove the platform and sensor and allow it to be moved between different areas of inspection.

FIG. 5 shows an alternative arrangement where the invention utilises two guide rails 925 and 925a in parallel, with the guide rollers 825 to carry platform 555 around the surface material 220 in order to conduct an inspection of the weld joint 210. The presents of at least two guide rollers 925(a) have an advantage in that they could potentially provide support for a larger weight of sensor(s). Two guide rollers 925(a) may require an elongate guide wheel 825 or a plurality of guide wheels to ensure that the platform maintains its orientation α° and keeps the sensor in a position to accurately record results.

In FIG. 3, there is shown a guide rail 200 that is constructed by the joining together a plurality of metal segments 201, coaxially mounted on a central wire 240. The segments 201 are threaded onto the wire 240 by the provision of a central hole (not shown) through each metal segment, allowing the user to select the length of the guide rail, as required. Each segment may have an additional hole in its side that allows the attachment of legs 210 and feet 215, the feet providing a means of attaching the guide rail to the surface of the material. The legs 210 give the ability to achieve the correct height for the use of the sensor.

The use of multiple segments 201 within this instantiation allows the guide rail 200 to be flexible. The rail 200 can be arranged to any conformation and then fixed and made rigid by the use of a spring 220 and securing nut 230 at the rear of the guide rail. By tightening the nut 230 the spring is compressed, which in turn pulls nut 231 towards nut 230 forcing the metal segments 201 together, providing a rigid, supportive guide rail 200. The guide rail may be tailored to a particular inspection area by removing the spring 220 and nut 230 and adding or subtracting metal segments prior to refitting both spring 220 and nut 230 and retightening.

FIG. 4 shows a plan orientation of the platform 450, which is constructed from a moulded plastic, with rubber guide rollers 750 located at their fixed positions. The use of a central channel 550 and two springs 650 allow the bias roller 751 to be biased towards the guide rollers 750. While no force is acting on the bias roller 751, the springs are compressed pulling the wheel close in line to the two guide rollers 750. When the user desires to attach/detach the platform from the guide rail, they simply apply force on the bias roller 751 to move it to its location away from the guide rollers 750. When in the desired position, the bias roller 751 is simply released and is allowed to return to its default location.

The invention claimed is:

1. A device suitable for structural health monitoring of a material, the device comprising:
   a guide rail, mountable on a surface of said material, wherein said guide rail comprises a plurality of segments coaxially mounted on a wire; and
   a platform comprising at least one sensor, wherein said platform is cooperatively engaged with said guide rail, when said platform traverses along the rail.

2. The device according to claim 1 wherein said guide rail comprises at least one leg support.

3. The device according to claim 2 wherein said at least one leg support comprises at least one fixing mount, to attach to said surface.

4. The device according to claim 3 wherein said at least one fixing mount is reversibly attached, such that it can be removed from the surface.

5. The device according to claim 4 wherein said at least one fixing mount is a magnet.

6. The device according to claim 1 wherein said guide rail is flexible.

7. The device according to claim 1, wherein said segments comprise a concave end and a convex end, such that segments cooperatively engage with each other.

8. The device according to claim 1 wherein said platform is reversibly cooperatively engaged with said guide rail.

9. The device according to claim 8 wherein said reversible engagement is provided by a bias roller and at least two guide rollers.

10. The device according to claim 8 wherein said reversible engagement is provided by a cooperatively engaged sleeve.

11. The device according to claim 8 wherein said reversible engagement is provided by one or more cooperatively engaged sleeves, a bias roller, and at least two guide rollers.

12. The device according to claim 1 wherein said at least one sensor comprises a distance measuring device.

13. The device, according to claim 12 wherein said distance measuring device is a click wheel, rotary encoder or string potentiometer.

14. The device according to claim 1 wherein said platform comprises a propulsion system, such as to automatically propel said platform along the guide rail.

15. A material inspection device, comprising:
- a flexible guide rail, mountable on a surface of material to be inspected, comprising a plurality of segments, wherein said segments are coaxially mounted on a wire, and upon tensioning the wire the segments are placed under compression and the guide rail becomes rigid; and
- a platform comprising at least one inspection sensor, wherein said platform is configured to cooperatively engage with said guide rail, such that said platform is moveable along the rail.

16. The device according to claim 15 wherein said guide rail comprises at least one leg support, and wherein said at least one leg support comprises at least one fixing mount, to attach to said surface, and wherein said at least one fixing mount is reversibly attached, such that it can be removed from the surface.

17. The device according to claim 16 wherein said at least one fixing mount is a magnet.

18. The device according to claim 15, wherein said segments comprise a concave end and a convex end, such that segments cooperatively engage with each other.

19. The device according to claim 15 wherein said platform is reversibly cooperative engaged with said guide rail, and wherein said reversible engagement is provided by (a) a bias roller and at least two guide rollers.

20. The device according to claim 15 wherein said platform is reversibly cooperatively engaged with said guide rail, and wherein said reversible engagement is provided by a cooperatively engaged sleeve.

21. The device according to claim 15 wherein said platform is reversibly cooperatively engaged with said guide rail, and wherein said reversible engagement is provided by one or more cooperatively engaged sleeves, a bias roller, and at least two guide rollers.

22. The device according to claim 15 wherein said platform comprises a motorized propulsion system, such as to automatically propel said platform along the guide rail.

23. A device suitable for structural health monitoring of a material, the device comprising:
- a guide rail, mountable on a surface of said material, wherein said guide rail comprises a plurality of segments, wherein said segments comprise a concave end and a convex end, such that segments cooperatively engage with each other; and
- a platform comprising at least one sensor, wherein said platform is cooperatively engaged with said guide rail, when said platform traverses along the rail.

24. The device according to claim 23, wherein said guide rail is flexible and wherein said platform is reversibly cooperatively engaged with said guide rail.

* * * * *